United States Patent [19]

Curry

[11] Patent Number: 4,974,929
[45] Date of Patent: Dec. 4, 1990

[54] FIBER OPTICAL PROBE CONNECTOR FOR PHYSIOLOGIC MEASUREMENT DEVICES

[75] Inventor: Kenneth M. Curry, Mission Veijo, Calif.

[73] Assignee: Baxter International, Inc., Deerfield, Ill.

[21] Appl. No.: 501,405

[22] Filed: Mar. 28, 1990

Related U.S. Application Data

[63] Continuation of Ser. No. 100,100, Sep. 22, 1987, abandoned.

[51] Int. Cl.$^5$ .............................................. G02B 6/16
[52] U.S. Cl. .............................. 350/96.29; 350/96.34; 350/96.2
[58] Field of Search ........................ 350/96.29–96.34, 350/96.2; 435/4, 7, 175; 128/635

[56] References Cited

U.S. PATENT DOCUMENTS

| | | | |
|---|---|---|---|
| Re. 31,879 | 5/1985 | Lubbers et al. | 436/133 |
| 3,223,686 | 12/1986 | Natta et al. | 260/80 |
| 3,542,662 | 11/1970 | Hicks et al. | 204/403 |
| 3,580,940 | 5/1971 | Webster | 260/448.2 |
| 3,612,866 | 10/1971 | Stevens | 250/71 |
| 3,847,553 | 11/1974 | Verbeck | 422/56 |
| 4,016,863 | 4/1977 | Brantigan | 128/632 |
| 4,173,495 | 11/1979 | Rapp et al. | 136/674 |
| 4,223,226 | 9/1980 | Quick et al. | 250/458 |
| 4,254,271 | 3/1981 | Finke et al. | 556/479 |
| 4,321,057 | 3/1982 | Buckles | 435/5 |
| 4,396,464 | 8/1983 | Giner et al. | 204/153.16 |
| 4,399,099 | 8/1983 | Buckles | 435/7 X |
| 4,476,870 | 10/1984 | Peterson et al. | 128/634 |
| 4,484,987 | 11/1984 | Gough | 204/1 T |
| 4,486,408 | 12/1984 | Kiel et al. | 435/175 X |
| 4,560,248 | 12/1985 | Cramp et al. | 350/96.34 |
| 4,568,518 | 2/1986 | Wolfbeis et al. | 422/56 |
| 4,587,101 | 5/1986 | Marsoner et al. | 422/56 |
| 4,680,268 | 7/1987 | Clark, Jr. | 128/635 X |
| 4,750,496 | 6/1988 | Reinhart et al. | 128/635 |

FOREIGN PATENT DOCUMENTS

| | | |
|---|---|---|
| 8703093 | 5/1987 | Denmark . |
| 0073558 | 9/1983 | European Pat. Off. . |
| 0091390 | 12/1983 | European Pat. Off. . |
| 0202055 | 11/1986 | European Pat. Off. . |
| 0212756 | 3/1987 | European Pat. Off. . |
| 2153102 | 8/1985 | United Kingdom . |

OTHER PUBLICATIONS

"Biosensors: Today and Tomorrow" by Ichinose, 5/86, Journal of Electrical Engineering, No. 233, pp. 80, 81, 87.

"Remote Detection of Organochlorides with a Fiber Optic Based Sensor II, A Dedicated Portable Fluorimeter" by Milanovich et al., vol. 15, No. 4, 1986 Analytical Instrumentation, pp. 347–358.

"Chemical Sensors Based on Fiber Optics" by Seitz, 1/84, Analytical Chemistry, vol. 56, No. 1, pp. 16A; 18A, 20A, 22A, 24A, 33A.

"Fiber Optic Chemical Sensors" Jan. 8, 1987 Release (Patent Pending).

"Fiber-Optic Sensors for Biomedical Applications" by Peterson & Vurek.

"Indwelling Blood Compatible Chemical Sensors" by Eberhart, 8/85, Surg. Clns. of North America; vol. 65, No. 4, pp. 1025–1040.

"Influence of Enzyme Concentration and Thickness of the Enzyme Layer on the Calibration Curve of the Continuously Measuring Glacose Optode" by Uwira et al., 1984, Advances in Experimental Medicine and Biology, pp. 913–921.

"Evidence for Boundary Layer Effects Influencing the Sensitivity of Nuroencapsulated $O_2$ Fluorescence Indicator Molecules" by Optitz and Lubbers, 1984, Adv. in Experimental Medicine and Biology, pp. 899–905.

*Primary Examiner*—John D. Lee
*Assistant Examiner*—John Ngo
*Attorney, Agent, or Firm*—Debra D. Condino

[57] ABSTRACT

A biological fiber optic probe chemical indicator device is disclosed. Structurally, the probe comprises at least one strand of optical fiber terminating in a coupling arrangement with a disposable sleeve assembly including a chemical indicator system for physiological substances. The disposable sleeve sensor element comprises a tubular housing with annular wall portions defining a female coupling channel means and a casing for a chemical reagent indicator.

16 Claims, 1 Drawing Sheet

FIBER OPTICAL PROBE CONNECTOR FOR PHYSIOLOGIC MEASUREMENT DEVICES

This is a continuation, of application Ser. No. 07/100,100 filed Sept. 22, 1987 (abandoned).

BACKGROUND OF THE INVENTION

The present invention relates to fiber optic probe device for bodily implantation for physiologic measurements of body fluid components and, more particularly, to the physiologic measurement of oxygen and glucose in blood or tissue.

Physiologic oxygen and glucose measurements are important for many reasons. The advantages of optical measurements of blood oxygen saturation levels during certain medical procedures, such as cardiopulmonary bypass heart surgery, are apparent. Equally important are physiologic measurements of glucose in blood tissue or serum to indicate metabolic malfunctions such as diabetes. Fiber optic devices for measurement of blood oxygen saturation are well known. In U.S. Pat. No. 3,807,390 to Ostrowski et al there is disclosed a fiber optic catheter for monitoring blood oxygen saturation in a human blood stream, in vivo, by insertion of the catheter tip into the cardiovascular system of the living body.

In U.S. Pat. No. 3,542,662 to Hicks et al there is described a bioelectrode for use in the determination of glucose in blood and serum. In this patented device an enzyme reaction is coupled to an electrode process. A glucose electrode consisting of a membrane of immobilized glucose oxidase is described. When the enzyme electrode is placed in contact with a biological solution or tissue, the glucose and oxygen diffuse into the enzyme layer with a corresponding outward flow of hydrogen peroxide and gluconic acid. The relationship between the oxygen saturation level and the amount of gluconic acid and peroxide present in the system is then calculated and the amount of glucose ascertained.

In U.S. Pat. No. 4,201,222 to Haase there is disclosed an optical catheter, including a fiber optic bundle, adapted to be inserted into a blood vessel of a living body for measuring the partial pressure of oxygen gas in the blood stream. The catheter comprises a semipermeable wall member for excluding the entry therethrough of blood liquid while permitting passage of blood gases. The intensity of a reflected visible light beam entering the optical fiber bundle, when compared to the intensity of the incident beam, corresponds to the partial pressure of the oxygen gas in the blood stream.

The present invention relates to a fiber optical device for the in vitro physiological measurement of oxygen and glucose by means of chemical sensors employing luminescent quenching mechanisms. The oxygen quenching of flourescent compounds is disclosed in U.S. Pat. No. 3,612,866 to Stevens where an apparatus for measuring the oxygen content of liquids or gases is described. The indicator mechanism is based on the molecular luminescent quenching effect of gaseous oxygen on aromatic flourescent compounds. Additionally, Lubbers et al in U.S. Pat. No. 4,003,707 describes an optical device for measuring physiologic oxygen in which the indicator element is the flourescent dye, pyrene butyric acid, which is quenched by oxygen molecules during use. Each of these devices is complex and is unconcerned with the size of the measuring device and replacement of the dye indicator systems.

Peterson et al in U.S. Pat. No. 4,476,870 describes an implantable fiber optic $PO_2$ biological probe comprising two strands of optical fiber terminating in a jacketed chemical indicator system. The indicator element contains a luminescent oxygen quenching dye, such as perylene dibutyrate, on an inorganic adsorbant support all packed in a tube, or envelope, of a gas permeable polymeric material. Light is introduced through one strand which light excites the jacketed dye to fluorescence. The flourescent and scattered light then exits through the other fiber optic strand to a measuring device to indicate the level of the oxygen quenching of the dye. While the Peterson et al device is both tiny and flexible for convenient bodily use, it suffers from the disadvantage that the adsorbed dye is ultimately lost through leaching into the fluid systems during use thereby requiring replacement of the entire structure.

Each of the above systems have advantages and disadvantages as applied to specific situations. In one or more of the systems, expensive and complex equipment is required especially in the case of glucose sensors. Moreover, even in the simple compact structures, such as that of Perterson et al, the optical system is integral and the total device must be replaced when the chemical sensor element becomes nonreusable. Therefore, there is significant interest in finding relatively simple physiological optical measuring devices in which the chemical sensor element is easily replaceable.

SUMMARY OF THE INVENTION

The present invention is an advancement in the art of biological fiber optical sensors for physiological measurements of body fluids, and overcomes many of the inadequacies and shortcomings of prior similar devices by its unique combination of novel features. Specifically, a specially designed disposable chemical sensor element comprised of a sleeve fitting to a fiber optic probe is provided which acts as the fiber optic terminal sensor over which body fluids flow as they are being monitored. Additionally, the novel chemical sensor sleeve design is employed to provide a novel dual probe catheter assembly for the measurement of physiological glucose and oxygen.

With the apparatus of the present invention a means is provided for readily obtaining a photometric analysis of body fluids with conventional photometric analysis equipment including a catheter intended for insertion into the bloodstream or tissue of a patient. Therefore, the apparatus includes a chemical sensor tip composed of a detachable sleeve connector which houses a reversible chemical indicator sensitive to specific components of body fluids. The sleeve connector is optically and physically coupled to an optical fiber which is the transmission source of entering and exiting illumination to the chemical indicator tip. The optical fiber is connected to photometric analysis equipment to interpret changes in the chemical indicator material caused by reactive components of particular body fluids impinging the sensor tip. Since it is critical that, during use, the indicator sleeve tip be immersed in the body fluids, as in the fluid flow stream in a catheter, it is desirable that the probe device be disposable for reasons of health and safety. Because the indicator sleeve of the present device is detachable it is conveniently and easily replaced with no disruption in use.

BRIEF DESCRIPTION OF THE DRAWINGS

The invention is illustrated by the accompanying drawings wherein.

DETAILED DESCRIPTION OF THE PREFERRED EMBODIMENTS

Although the present optical sensor finds its principal use in the measurement of physiological oxygen saturation, it may be satisfactorily applied to the measurement of other physical phenomena which exhibit similar behavior and meet the criteria to be developed herein. A device for the measurement of physiological oxygen and glucose will be used as an illustrative example and preferred embodiment.

Figure 1:
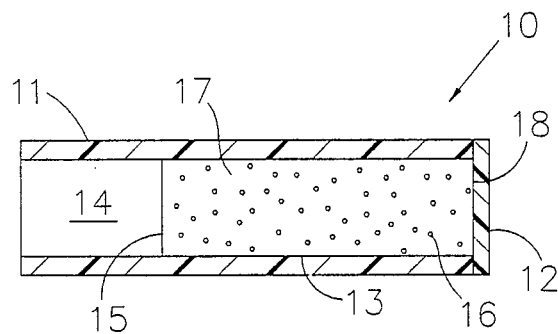
FIG. 1 is a front cutaway view of an optical sensing sleeve connector of the present invention having a chamber for housing a chemical indicator for body fluid constituents.

FIG. 1 shows a longitudinal cross section of optical sleeve sensor connector element 10 of the present invention. The connector 10 is a cylindrically shaped element comprising a sheath 11 and end cap 12 defining a cavity 35 filled with an optically active chemical indicator material 13 generally comprising a dye or luminescent material which interacts with physiological components in a biological environment. Also shown is interior passageway cavity 14 which is an annular channel acting as the female receptor for a terminating strand of optical fiber (not shown). The diameter of cavity 14 is of a size commensurate with, or substantially the same as, the core of an optical fiber so as to snuggly receive the fiber and thereby effect an abutment and optical coupling with the encapsulated optically active material 13 at the interface junction 15. Therefore, the tip of any optical fiber should be firmly against the chemical indicator material element 13 at interface junction 15.

As shown, sleeve connector 10 is an oxygen gas sensor and the indicator material 13 is composed of an oxygen quenching flourescent dye 16 dispersed in a polymeric matrix 17. Additionally, sheath 11 as the cladding for the oxygen sensitive fluorescent dye material 13 is comprised of a gas permeable material such as well known hydrophobic expanded polypropylene and silicon polymers. The tip 12 is that element of the structure which will confront and come into contact with biological fluid flow, as in a catheter encountering blood, tissue or serum, and must be comprised of gas permeable material also. While illustrated as a separated element, endcap 12 may be integral with sheath 11 and comprise the same material or be composed of a different gas permeable composition. If endcap 12 is the same gas permeable material as the sheath 11, it is preferably in a thinner form such as a membrane.

Suitable examples of oxygen quenching dye materials to be used in indicator element 13, include silicone dye fluorescent polymer materials in copending applications Ser. No. 07/047,690 to Oviatt et al (U.S. Pat. No. 4,746,751), and Ser. No. 07/000,537, to Hsu et al (U.S. Pat. No. 4,714,770) respectively. Other examples include fluorescent dye pyrene butyric acid in bis-2-ethyl-heylphtalalate. Still further examples include perylene and benzoperylene embedded in room temperature vulcanizable silicone polymers. Because the instant fiber optical sleeve connectors are replaceable, it is not essential that the indicating oxygen quenching fluorescent dye be so embedded in or chemically bonded to the polymer matrix to avoid dye leaching. Consequently, the dyes or luminescent materials can be absorbed or otherwise mixed with polymeric binder materials.

The sheath material 11 and the polymer matrix 17 of indicator element 13 may be comprised of any gas diffusable hydrophobic material such as silicon polymers, polyesters, or any gas permeable synthetic plastic material. A preferred sheath material II is porous expanded polypropylene tubing sold under the trademark "CELGARD", by the Celanese Corporation. Other preferred polymers include tetrafluroethylene and poly-dimethyl siloxane.

Figure 2:
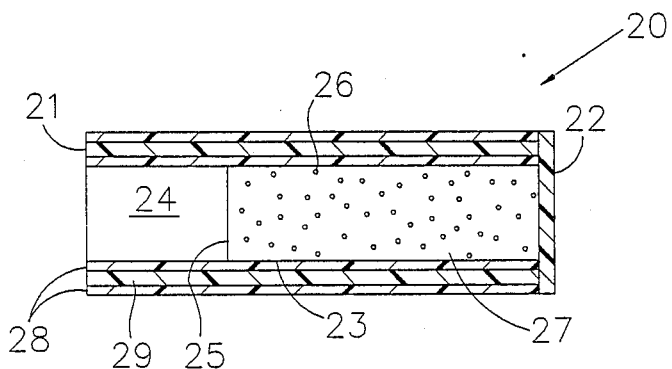
FIG. 2 is a front sectional view of another embodiment of an optical sensing sleeve connector which employs a multilayered envelope for the chemical indicator to render it useful in the measurement of physiological glucose.

FIG. 2 demonstrates another embodiment of the present invention in the form of a multilayered tubular glucose indicator sleeve 20 of the present invention wherein 24 is the same fiber optic probe receptor channel as in FIG. 1. Likewise female receptor channel 24 terminates and interfaces at 25 with the chemical indicator filled portion 23 which is identical with chemical indicator element 13 of FIG. 1. The sheath or cladding portion designated as 21 functionally corresponds to sheath element 11 of FIG. 1 but comprises a multilayered cladding for the chemical indicator 23. Directly enveloping the indicator portion 23 are thin cylindrical walls of a gas permeable polymeric material, such as expanded polypropylene, and herein designated as interlayer 28. Overcoated on interlayer 28 is sandwich layer 29 which is a glucose conversion layer and comprises glucose oxidase dispersed in a polymer matrix or cross linked with glutaraldehyde. Overlaying and jacketing the entire cylindrical portion of the glucose connector sleeve 20 is an overlayer 28 of gas permeable material such as expanded polypropylene, said overlayer also being designated 28. End capping the element 20 is material 22 which is identical to that described for element 12 of FIG. 1. The slidable female interaction of a fiber optic core with cavity 24 to form an optical interface connection with the encapsulated chemical indicator 23 at junction 25 is identical with the linkage description given for FIG. 1.

Figure 3:
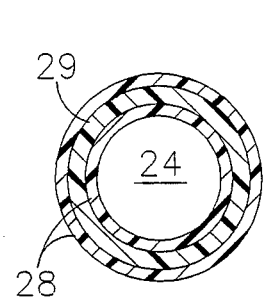
FIG. 3 is a cross sectional view demonstrating an end view perspective of the chemical indicator portion of FIG. 2.

The tubular shape of FIG. 2 is more aptly demonstrated in FIG. 3 where a cross sectional view is shown demonstrating the multilayered cladding 21 and receptor cavity 24. As can be appreciated, the cavity 24 and the indicator material (not shown) is circumferentially wrapped by the gas permeable interlayer and overlayer 28 and sandwich layer 29, the glucose oxidase catalyst. It is this layered tubular structure which enables effective operation of a dual probe glucose sensor catheter to be hereinafter described.

An oxygen gas indicator sleeve of FIG. 1 is prepared in the following manner. Two centimeter lengths of "CELGARD" expanded polypropylene hollow tubing of 240 micron diameter are cut. An oxygen quenching dye indicator composition comprising Ru(4,7-Diphenyl-1,10-phenanthroline)$_3$ Cl$_2$ and uncured polydimethylsiloxane Cl$_2$ and uncured polydimethylsiloxane crosslinked binder is provided in a syringe. The annular channel of the polypropylene tubing is filled to three quarters capacity with the dye composition and allowed to cure. One of the open ends of the tubing is trimmed with a razor blade to reveal a continuous circular cross-section of the polypropylene and dye indicators. The continuous end piece is dipped in a one part polydimethylsiloxane sealant and allowed to cure thereby creating a membrane end cap, corresponding to element 12 of FIG. 1, on the tubular element. There is provided a fiber optic sleeve connector device having an open cavity receptor end and a closed channel having an oxygen indicator dye composition encased therein.

A strand of optical fiber of approximately 230 microns is slidably inserted into the receptor channel (cavity 14 of FIG. 1) of the prepared sleeve connector to effect optical coupling at the interface (15 of FIG. 1) of the dye indicator portion (element 13 of FIG. 1). Optionally, and preferably, the strand of optic fiber can be connected to the receptor channel 14, after insertion, and before curing of the dye composition, to create an integral and non-removable optical probe coupling. In this manner this fiber makes direct contact with the uncured dye composition and forms a fused optical interface coupling (element 15 of FIG. 1) with the dye indicator portion of the connector. When this procedure is used, the gas porous endcap is applied after linkage of the fiber and sleeve connector.

To prepare the glucose indicator of FIG.2 a 440 micron Celgard hollow polypropylene tubing is provided and razor cut into approximately four inch segments. For the immobilized enzyme layer, solutions of gluteraldehyde, glucose oxidase, catalase, and bovine serum albumin are prepared in a conventional manner using mixed acetate buffered solutions of glutaraldehyde. The enzyme immobilization by glutaraldehyde in a bovine serum albumin (BSA) matrix was carried out by techniques outlined by Thomas et al in Biochimie, Vol. 55, pages 229-244, Monoenzymatic Model Membranes, hereby incorporated by reference. The enzyme solution is then placed in a syringe and applied by needle to the annular channel of the polypropylene tubing to completely fill the inner space. Before curing of the enzyme solution, an uncoupled oxygen sensor sleeve prepared in the manner outlined above, is then inserted in the larger tubing and the curing of the enzyme layer completed. There results the formation of a glucose sensor sleeve connector conforming to FIG. 2 which can be physically and optically coupled to an optic fiber strand. Again, as in the case of the oxygen sensor prepared above, an integral oxygen sensor fiber optic probe could be prepared and inserted into the larger polypropylene tubing with the uncured enzyme layer to form an integral glucose sensor probe.

As indicated, the sensor sleeve connector elements of FIGS. 1 and 2 are gas permeable, being formed from lengths of hollow gas permeable tubing which are filled with fluorescent dye or luminescent material thereby forming fluoroscent transducers 13 and 23. The length of the transducer is such that incoming light causes excitation of the fluorescent indicator material with consequent re-emission of light through the optical fiber. Because the degree of oxygen quenching effects the fluroescent material, the re-emitted light can be correlated to oxygen concentration in the indicator and measurement of same.

In operation, the fiber optic glucose sensor of FIG. 2 is brought into contact with blood or serum fluid containing a concentration of glucose and oxygen. Both the glucose and the oxygen diffuse through the gas permeable layers of sheath 2 while only oxygen can diffuse through the hydrophobic endcap, 22. The oxygen continues on into the fluorescent dye polymer layer where it quenches an oxygen quenching fluorescent dye. The glucose and oxygen in the fluid comes in contact with the immobilized glucose oxidase layer 29 which contains catalyst thereby promoting the following reactions:

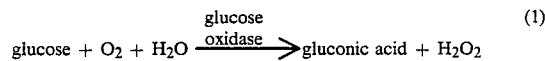

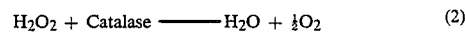

A certain portion of the oxygen diffusing through the sleeve connector 20 is consumed by reaction with glucose catalyzed by the enzyme in layer 29 and, therefore, remains unavailable for detection by the oxygen quenching fluorescent dye in 23. In order to calculate accurate concentrations of glucose, an oxygen sensor is required as a reference sensor to read the concentration of oxygen that would have been detected had no enzyme reaction occurred in the glucose sensor of FIG. 2. With the appropriate compensatory factoring, the difference in oxygen detected will be proportional to the glucose concentration which will be so calculated.

However, for the system to provide useful results, the glucose concentration, as opposed to oxygen concentration, must be the limiting factor. Since the reaction is limited stoichiometrically by whichever component is present in the lowest concentration, a thin membrane composed of medical grade polyurethane, commercially available from Thermedics, Inc., under the Trademark "TECOFLEX", is placed around the outer sheath of the glucose probe to limit the flux of glucose, but not the flux of oxygen, into the glucose sensing portion of the dual probe device. In this way, it is possible to ensure that the desired analyted glucose is always present as the limited species.

Figure 4:
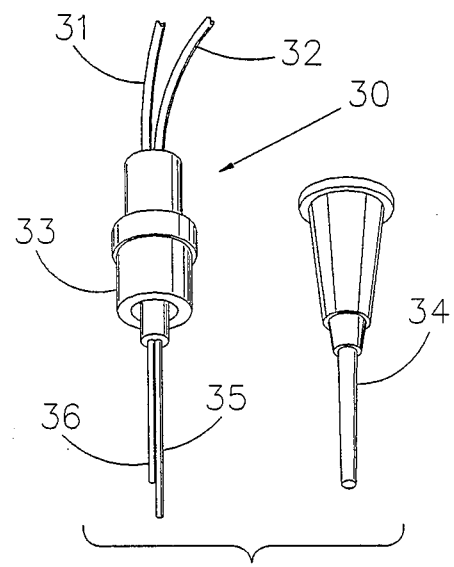
FIG. 4 is another embodiment of the present invention and demonstrates a front sectional and segmented view of a dual probe catheter employing the sleeve connector structures of FIGS. 1 and 2.

The optimum use of the sleeve connectors depicted in FIGS. 1 and 2 is in a dual probe glucose-oxygen sensor. FIG. 4 illustrates a novel dual probe catheter assembly 30 utilizing the sleeve connectors of the present invention. There is demonstrated the essential workable components of a dual probe catheter assembly 30 where the two optical fibers are indicated by numerals 31 and 32 being drawn and connected to a spectral analyzer (unshown), the fiber optic strands being sheathed or covered before the entrance into the housing head 33. As shown, the two fibers are drawn together through an orifice (not shown) and are encased by tubular catheter 34 separately shown in the drawing. The tips or terminals 35 and 36 of the drawn dual strands of optical fibers are optically coupled to the flourescent oxygen and glucose sensor elements shown in FIGS. 1 and 2 in a manner described above.

The sleeve sensors are then encased in the tubular catheter 34 which is securely attached to the housing 33. The tubular catheter 34 is then inserted directly human or animal body whereby the oxygen and glucose sensor elements come into direct contact with the blood or serum to be analyzed. The indicator elements attached to terminals 35 and 36 come into direct contact with the particular blood or serum causing emitted light from the chemical indicators of the probes to be affected in the manner described above. The spectral data from each fiber optic strand is measured and analyzed for the oxygen and glucose content of the specimen as indicated by the respective tubular terminal probes.

The optical fitting structures and optical probe structures of the present invention may be conveniently manufactured in large quantities and assembled together with selected sensors to provide a plurality of devices for optically measuring a sample of material undergoing optical fiber probe analysis. The various members of optical fitting interfacing structures so manufactured can then be used interchangeable with one another. Uniform geometries of optical fibers ensure optical coupling at the optical interface between the optical fiber and the chemical indicator element. The optical fitting interfacing structures of the present invention thus have wide applicability in situations where a number of fiber optical measurements or analysis must be accurately and rapidly performed.

It will be appreciated that the optical sleeve connector of the present invention permits a conventional catheter type input to photometric analysis equipment to be continuously and repeatedly used in making photometric analysis of physiologic components of body fluids.

The novel features which are considered characteristic for the invention are set forth in particular in the appended claims. The invention itself, however, both as to its construction, its method of operation, together with the additional objects and advantages thereof, will best be understood from the following description of specific embodiments when read in connection with the accompanying drawings.

What is claimed is:

1. A sensor connector for the measurement of a fluid or gaseous constituent comprising:
    a housing permeable to said constituent and defining an annular channel therein, said channel containing a reagent reactive with said constituent to produce a by-product;
    an exterior sleeve for limiting the rate of influx of the constituent; and
    said housing also comprising a layer permeable to said by-product interior to said annular channel and defining an interior chamber, said interior chamber containing a chemical optically responsive to said by-product for measurement of the concentration of said fluid constituent via said by-product.

2. A sensor connector according to claim 1 wherein the constituent is glucose, the housing comprises a gas-permeable material and the renewable reagent is a catalyst.

3. A sensor connector according to claim 2 and wherein the catalyst is glucose oxidase, the permeable layer is permeable to oxygen gas, the by-product is oxygen, and the reagent for optical measurement is an oxygen-quenched fluorescent dye.

4. A sensor connector according to claim 3 and wherein the gas-permeable materials are selected from the group consisting of polypropylene, tetrafluoroethylene, and polydimethylsiloxane.

5. A sensor connector according to claim 4 and wherein the sleeve for limiting the influx of glucose is comprised of polyurethane.

6. A sensor connector according to claim 5 and wherein the glucose oxidase is immobilized by crosslinking with glutaraldehyde.

7. A sensor connector according to claim 6 and further comprising a fiberoptic core abutting said chemical for optical transmission to and from said reagent.

8. A sensor connector according to claim 7 and wherein the oxygen-quenched fluorescent dye is comprises $Ru(4,7,-diphenyl-1,10-phenathroline)_3Cl_2$ in polydimethylsiloxane.

9. A fiber optic sensor comprising:
    a fiber optic core;
    a sensor connector comprising a first layer permeable to a chemical to be measured and defining an interior chamber, only a portion of which is filled with an optically active indicator for said chemical, the remainder of the chamber forming an open receptor cavity generally in the shape of the core so that the fiber optic core is attached to the sensor by insertion in the cavity before use and detached after use to maximize repeated use of the fiber optic core.

10. A fiber optic sensor according to claim 9 and wherein the sensor connector further comprises:
    a reagent reactive with a constituent to be sensed, said reagent located exterior to said first layer; and
    a second layer of material permeable to said constituent exterior to said reagent; and
    wherein said first layer is permeable to a by-product of the reaction of said constituent with said reagent so that said optically active indicator indicates the presence of said by-product.

11. The fiber optic sensor of claim 10 wherein the sheath housing further comprises immobilized glucose oxidase external to said polymer and an overlayer of gas permeable material.

12. The fiber optic sensor of claim 11 wherein the gas permeable polymer layers are selected from the group of polymers consisting of polypropylene, tetrafluoroethylene, and polydimethylsiloxane.

13. The fiber optic sensor of claim 11 wherein the immobilized glucose oxidase layer comprises glucose oxidase crosslinked with glutaraldehyde.

14. A sensor connector according to claim 11 and wherein the oxygen-quenched fluorescent dye comprises $Ru(4,7,-diphenyl-1,10-phenanthroline)_3Cl_2$ in polydimethylsiloxane.

15. A fiber optic sensor according to claim 11 and wherein the sensor connector includes an exterior sleeve for limiting the rate of influx of the constituent.

16. The fiber optic sensor of claim 9 wherein the sheath housing comprises a gas permeable polymer sheath and tip and the indicator is an oxygen-quenched fluorescent dye.

* * * * *

UNITED STATES PATENT AND TRADEMARK OFFICE
CERTIFICATE OF CORRECTION

PATENT NO.    : 4,974,929

DATED         : December 4, 1990

INVENTOR(S)   : Kenneth M. Curry

It is certified that error appears in the above-identified patent and that said Letters Patent is hereby corrected as shown below:

Column 6, line 16, delete "Catalase" and insert --Catalyst--.

Column 6, line 16, delete "———" and insert -- ⟶ --.

Column 7, line 31, insert --be-- after "best".

Signed and Sealed this

Thirteenth Day of October, 1992

Attest:

DOUGLAS B. COMER

*Attesting Officer*   Acting Commissioner of Patents and Trademarks